May 15, 1973 T. G. HARCHARIK ET AL Plant Pat. 3,335
AZALEA PLANT
Filed Aug. 25, 1971
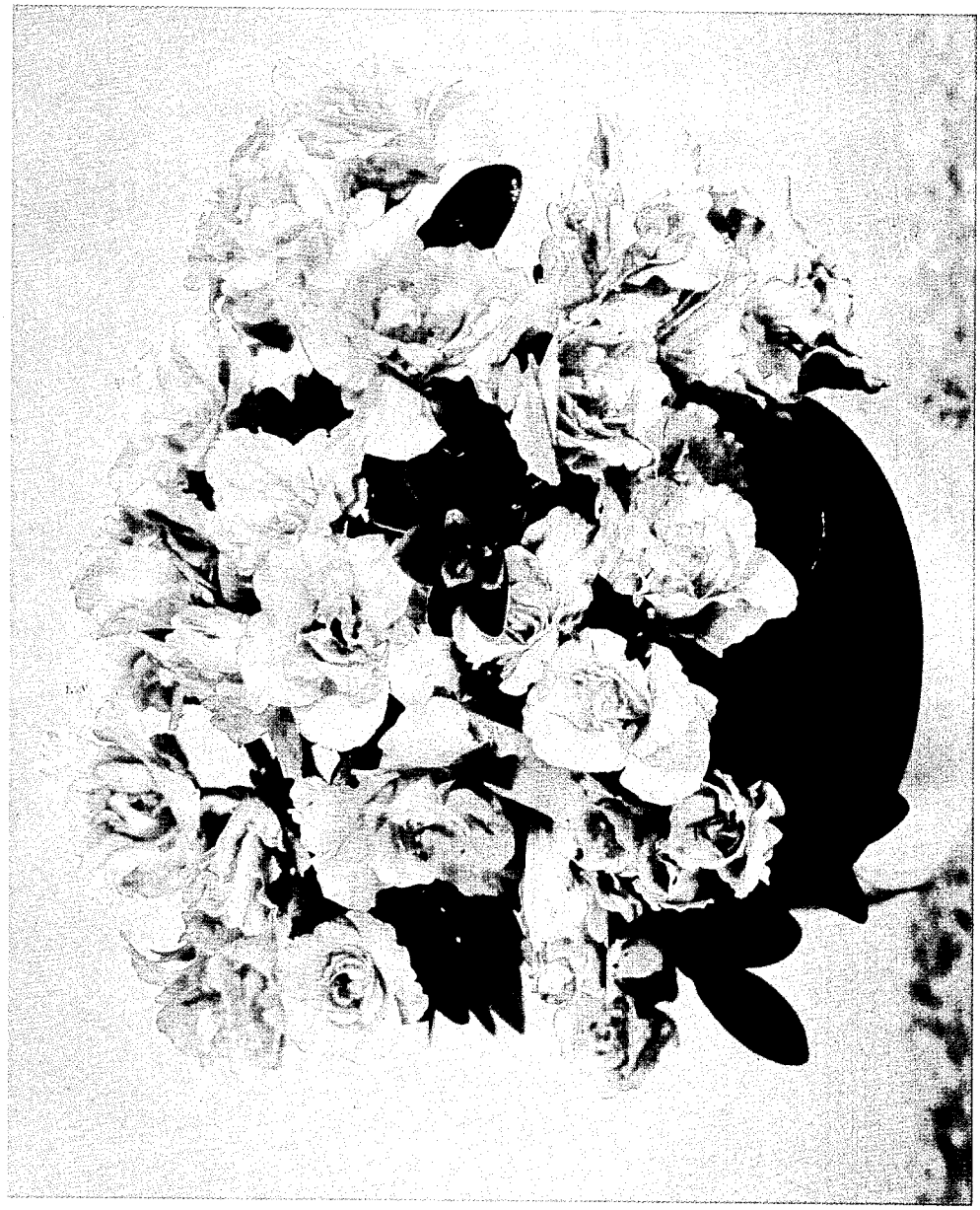

United States Patent Office

Plant Pat. 3,335

Patented May 15, 1973

3,335
AZALEA PLANT

Thomas G. Harcharik, Salinas, Calif., and Walter W. Knicely, Barberton, and William E. Duffett, Akron, Ohio, assignors to Yoder Brothers, Inc., Barberton, Ohio

Filed Aug. 25, 1971, Ser. No. 175,013
Int. Cl. A01h *5/00*
U.S. Cl. Plt.—57 1 Claim

The present invention comprises a new and distinct variety of azalea pant which has resulted from a spontaneous mutation on the unpatented azalea cultivar known as Whistler.

The new variety is similar in many respects to Whistler, having the same characteristics of:

(1) Semi-double flower form.

(2) Each floret unfurling slowly from the bud stage and closely resembling a minature hydride tea rose.

(3) Mid to late season response with 3–4 weeks keeping quality in the home.

The new variety is distinguished from Whistler by its medium pink color as compared with the orchid pink color of Whistler.

Varietal worth was determined by flowering liners from cuttings taken from the initial selection in both a year-round and natural season developmental flowering program over a period of three years. Stock growth was evaluated in the vicinity of southern Florida.

The new variety has been asexually reproduced by cuttings at Barberton, Ohio, and has been found to retain its distinctive characteristics through successive propagations.

The new variety when grown in the vicinity of Barberton, Ohio has a response described as mid to late, and the following detailed description is based on observations made of the new variety in a greenhouse in Barberton, Ohio. The response time and blooming period may vary significantly with varying environmental condictions such as temperature, light intensity and daylength. Suggested flowering period is from mid-January through early May in a natural season program. It is not recommended in a year-round controlled program.

The accompanying drawing illustrates the new variety, with the colors being as nearly true as possible with color photographs of this type.

The following is a detailed description of the new variety. Color references are to the Munsell Color Book, 1963 edition, and comparisons made with the parent cultivar Whistler. Where only a single value or description appears for the new cultivar, the same value or description applies to the parent cultivar as well.

BOTANICAL CLASSIFICATION: *Rhododendron hybrida evergreen type*

| | Pink Whistler | Whistler |
|---|---|---|
| Flower: | | |
| Color (Spring color in Barberton, Ohio): | | |
| General tonality | Medium pink, nearest to 5RP6/12 but lighter | Orchid pink, near 3.75RP5/12. |
| Sepals first | Grayish medium pink, near 7.5RP6/8 | Light orchid pink, near 2.5RP6/10. |
| Petals unfurl | Medium pink, nearest to 5RP6/12 but lighter | Orchid pink, near 3.75RP5/12. |
| Fully open: | | |
| Inside | do | Do. |
| Reverse | do | Do. |
| Base of petals | Light salmon pink, near 7.5RP8/6 | |
| Imperfect outer hose | Medium pink near 5RP6/12 but lighter, blending to light salmon pink near 7.5RP8/6. | Orchid pink near 7.5RP8/6 blending to light salmon pink near 7.5RP8/6. |
| Variations: | | |
| Dotted | Rose, near 7.5RP5/12 | Rose, near 7.5RP4/14. |
| Bud: | | |
| Size | Medium | |
| Form | Conoidal | |
| Opening habit | Each floret unfurls slowly from the bud stage closely resembling a miniature hybrid tea-rose. Fully open flowers are cup-like. | |
| Bloom: | | |
| Size | Medium | |
| Average | 2½" | |
| Range | 1¾"–3" | |
| Borne | Several together | |
| Average | 2½ | |
| Range | 1–4 | |
| Form | Double stamen, generally completely petaloid with an imperfect outer hose. | |
| Blooming habit | Once profusely | |
| Response | Mid-late | |
| Natural season | Mid-January thru early May | |
| Sepals "bud sheath" | Smooth, hairy, deciduous | |
| Calyx | Imperfect hose | |
| Peduncle: | | |
| Length | Long | |
| Aspect | Hairy | |
| Strength | Strong | |
| Petals: | | |
| Texture | Smooth, flat | |
| Appearance: | | |
| Inside | Satiny | |
| Outside | do | |
| Form | Rounded and notched | |
| Arrangement | Imbricate | |
| Fragrance | None | |
| Persistence | Non-shattering | |
| Longevity: | | |
| Greenhouse | 3–4 weeks | |
| Home | 4–5 weeks | |
| Reproductive organs: | | |
| Stamen | Generally 5 and mostly petaloid | |
| Anthers | Reddish brown, near 2.5R4/8 | |
| Filaments | Generally petaloid, medium pink, near 5RP6/12 | Generally petaloid, orchid pink, 3.75RP5/12. |
| Style | Normal columnar, rose, near 7.5RP5/14. | |
| Stigma | Normal, dark reddish brown, near 2.5R3/10 | |
| Ovaries | Hypogynous | |
| Fruit | None | |

TABLE—Continued

| | Pink Whistler | Whistler |
|---|---|---|
| Foliage: | | |
| Type | Evergreen | |
| Leaflets | Single | |
| Size—length | 1½" | |
| Range | 1"-2" | |
| Width | ⅞" | |
| Range | ½-1½" | |
| Shape | Ovate | |
| Texture | Waxy | |
| Rib and mid veins | Slightly depressed | |
| Edge | Smooth | |
| Color—new foliage: | | |
| Upper | Yellow-green, near 5GY5/6 | |
| Lower | Yellow-green, near 5GY6/6 | |
| Mature foliage: | | |
| Upper | Green, 7.5GY3/4 | |
| Lower | Gray-green, near 7.5GY5/4 | |
| Petiole | Short, yellow-green, near 5GY6/6 | |
| Plant | Bush | |
| Growth habit | Semi-upright, compact | |
| Breaking habit | Medium vigorous | |
| Size of average finished product from a standard No. 7 liner of Yoder Brothers, Inc., Barberton, Ohio: | | |
| Height | 10-12" | |
| Diameter | 10-12" | |
| Rooting habit | Good | |
| Budding ease | do | |
| Uniformity of budding | do | |
| Growth regulator | Not required | |
| Stems (color): | | |
| New wood | Yellow-green, 5GY7/8 | |
| Mature wood | Brown, 10YR4/6 | |
| Responsiveness to day length and temperature. | Buds quickly at 65° night temperature or above, though a longer period of development time is needed to fully mature buds for forcing; therefore variety is timed as a mid to late season cultivar. Will become vegetative when grown below 65° N.T. | |
| Resistance to Cylindrocladium | Fair-good | |
| Cooler tolerance | Excellent | |
| Shipping tolerance | Good | |
| Recommended flower period | Natural season only—mid-January thru April | |

We claim:

1. A new and distinct variety of azalea characterized particularly as to uniqueness when compared to its parent cultivar Whistler by its attractive medium pink color.

No references cited.

ROBERT E. BAGWILL, Primary Examiner

UNITED STATES PATENT OFFICE

CERTIFICATE OF CORRECTION

Patent No. PP-3,335 Dated May 15, 1973

Inventor(s) THOMAS G. HARCHARIK; WALTER W. KNICELY and WILLIAM E. DUFFETT

It is certified that error appears in the above-identified patent and that said Letters Patent are hereby corrected as shown below:

In the table, line 13, opposite "Dotted" under "Pink Whistler" change "7.5RP5/12" to --7.5RP4/12--.

Signed and sealed this 1st day of October 1974.

(SEAL)
Attest:

McCOY M. GIBSON JR.
Attesting Officer

C. MARSHALL DANN
Commissioner of Patents